United States Patent [19]

Sadhir et al.

[11] Patent Number: 5,288,643
[45] Date of Patent: Feb. 22, 1994

[54] QUICK METHOD TO DISTINGUISH ALKYLBENZENE AND NAPHTHENIC LUBRICANTS IN COMPRESSORS

[75] Inventors: Rajender K. Sadhir, Plum Boro, Pa.; Sung L. Kwon, Burnsville, Minn.

[73] Assignee: Thermo King Corporation, Minneapolis, Minn.

[21] Appl. No.: 85,063

[22] Filed: Jun. 29, 1993

[51] Int. Cl.$^5$ .................. G01N 31/00; G01N 33/03
[52] U.S. Cl. .................................... 436/60; 436/139; 436/140; 436/141; 422/61
[58] Field of Search ............... 436/60, 140, 141, 139, 436/808; 422/61; 215/32

[56] References Cited

U.S. PATENT DOCUMENTS 4,203,725  5/1980  Snowden .................. 436/60
4,744,870  5/1988  Kauffman ................. 204/1
5,229,295  7/1993  Travis ..................... 436/39

OTHER PUBLICATIONS

Merck Index, 11th Edition, Merck & Co., Inc., (1989), p. 1150.

Primary Examiner—James C. Housel
Assistant Examiner—N. Bhat
Attorney, Agent, or Firm—M. J. Moran

[57] ABSTRACT

A method for the identification of whether a lubricant in a compressor is an alkylbenzene or a naphthenic oil. This method comprises adding 3,3-bis (p-hydroxyphenyl) phthalide and observing whether there is an absence or presence of turbidity.

4 Claims, No Drawings

QUICK METHOD TO DISTINGUISH ALKYLBENZENE AND NAPHTHENIC LUBRICANTS IN COMPRESSORS

BACKGROUND OF THE INVENTION

This invention relates to a novel method of distinguishing lubricants utilized in compressors. Lubricants have been used in compressors generally to protect the frictionally engaged components therein from wear. More particularly, this invention relates to a simple yet accurate method of distinguishing between an alkylbenzene and a naphthenic lubricant which are widely used as lubricants in compressors. Thus, for example, lubricants have been used in conjunction with refrigerants in compressors of mobile refrigeration systems. Earlier on naphthenic oil, such as Suniso 3GS was widely used. Lately, an alkylbenzene such as Zerol-150 (Shrieve Chemicals) has been used exclusively. Chemically, the naphthenic oils are completely saturated hydrocarbons consisting of cyclic structures e.g. cycloparaffinic molecules. Alkylbenzenes contain aromatic rings with branched hydrocarbons having a general formula as shown in FIG. 1:

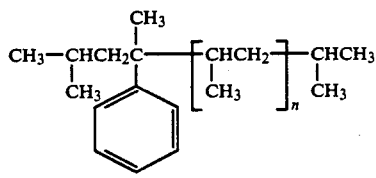

FIG. 1 in which n is a positive integer.

They are prepared for example by the known Friedel-Crafts reaction such as by alkylation of benzene with alkylchlorides or olefins.

Commercial manufacturers of refrigeration systems such as Thermo King has used alkylbenzenes as a lubricant in combination with fluorocarbon refrigerants available under the tradename R-12, R-22, R-500 and R-502 within the last decade. However, it is estimated that there are about a half-million refrigeration systems currently in use which have utilized both types of lubricants.

There is no easy and quick method of distinguishing which of these two lubricants are used in the system. The present practice is to withdraw a lubricant sample from the compressor and bring it to the laboratory for analysis. Most common method presently used to distinguish these two types of compounds relies on a spectroscopic technique (infra-red spectrophotometer) which gives distinct absorption peaks due to aromatic benzene at 1600 cm[1] in alkylbenzene lubricants.

With the recent legislative changes, which prohibits the use of high Ozone Depletion Potential (ODP) and high Global Warming Potential (GWP) refrigerants, refrigerants such as R-12 which is dichloro difluoro methane has to be replaced by compounds such as MP-66 which is a ternary blend of chloro difluoro methane, difluoro ethane and tetrafluoro ethane or R-134a which is tetrafluoro ethane. It has been concluded that while R-134a will be suitable for new compressors, it may not be economically feasible to retrofit the existing compressors with R-134a, because of certain compatibility problems. Refrigerant MP-66 has been suggested as a suitable replacement of R-12 in existing compressors. The lubricant of choice with MP-66 is alkylbenzene. Therefore, it is important for manufacturers of refrigeration systems to find out the type of oil in the existing compressors. The primary reasons to learn the identity of the lubricant are:

a. Savings—if the existing lubricant turns out to be alkylbenzene, then one needs to replace only R-12 refrigerant with MP-66, without changing the lubricant.

b. If the lubricant is a naphthenic oil, then one would need to replace both the refrigerant and lubricant with MP-66 and alkylbenzene to avoid any compatibility problems.

SUMMARY OF THE INVENTION

According to the present invention, there is provided a novel yet facile method for the rapid identification of which type of lubricant has been used in a compressor.

Briefly, the method comprises adding a small but sufficient amount of 3,3-bis (p-hydroxyphenyl) phthalide to a small sample containing either an alkylbenzene or a naphthenic oil lubricant. If turbidity occurs instantaneously, it indicates a naphthenic oil. In contrast, if no turbidity occurs, it indicates the presence of an alkylbenzene.

DETAILED DESCRIPTION OF THE INVENTION

The method according to the present invention comprises first withdrawing a small sample typically about 5 ml of the lubricant from a compressor into a suitable container such as a test tube.

In a separate vessel sufficient amount of 3,3-bis(p-hydroxyphenyl) phthalide of the formula 2:

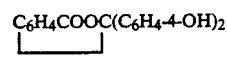

is dissolved in sufficient amount of alcohol yielding a 1% w/v solution.

The above compound also known as phenolphthalein is widely available. Please see for example Merck Index 11th Edition, page 1150, reference number 7208.

A sufficient amount of the above compound in alcohol to produce turbidity with a naphthenic oil is then added to the test tube containing the sample of lubricant. After the addition, the test tube is shaken. The resulting solution is then compared against a blank. If it turns opaque or produces turbidity, it indicates the presence of naphthenic oil in the sample. If no turbidity develops it indicates the presence of an alkylbenzene.

In a typical practice according to the present invention, from about 0.2 to about 5.0 ml and preferably from about 1 to 3 ml of the 1% w/v solution of 3,3-bis(p-hydroxyphenyl) phthalide is added to about 5 ml of the test sample. The resulting solution is shaken and it is compared against a blank or control to determine if any turbidity has developed.

The blank or control may comprise water but typically it is the same 3,3.bis (p-hydroxyphenyl) phthalide solution in alcohol.

In a commercial embodiment according to the present invention, the 1% w/v of 3,3-bis (p-hydroxyphenyl) phthalide solution is dispensed in unit dosage form. Typically from about 1 ml to about 5 ml is dispensed into plastic or glass ampules. The ampules are then sealed.

In use, the end user breaks off the seal and add the requisite amount of the alcoholic solution to the sample containing the lubricant. As described previously, the occurrence of turbidity indicates a naphthenic oil. The lack of turbidity indicates an alkylbenze.

The following Example is included to further illustrate the practice of this invention.

Five different lubricants (two synthetic alklybenzene and three naphthenic type) were selected for this experiment details of which are shown in Table 1.

TABLE 1

| Sample No. | Lubricant I.D. | Supplier | Type |
| --- | --- | --- | --- |
| 1 | Zerol-150 | Shrieve | Alkylbenzene |
| 2 | Suniso-3GS | Witco | Naphthenic |
| 3 | Zerice Supreme-32 | Exxon | Naphthenic |
| 4 | Compoil 200 | B.V. Associates | Naphthenic |
| 5 | Zerol-300 | Shrieve | Alkylbenzene |

The following Table 2 sets forth the results after the addition of 3,3-bis (p-hydroxyphenyl) phthalide.

TABLE 2

| Sample No. | Lubricant | Amount of 1% (ml) 3,3-bis-(p-hydroxyphenyl)-phthalide | Color |
| --- | --- | --- | --- |
| 1 | 5 ml Zerol 150 | 2 | Transparent No change |
| 2 | 5 ml Zerol 150 | 1 | Transparent No change |

TABLE 2-continued

| Sample No. | Lubricant | Amount of 1% (ml) 3,3-bis-(p-hydroxyphenyl)-phthalide | Color |
| --- | --- | --- | --- |
| 3 | 5 ml Zerol 150 | 0.5 | Transparent No change |
| 4 | 5 ml Zerol 150 | 0.2 | Transparent No change |
| 5 | 5 ml Suniso 3GS | 2.0 | Opaque, White |
| 6 | 5 ml Suniso 3GS | 1.0 | Opaque, White |
| 7 | 5 ml Suniso 3Gs | 0.5 | Slightly Opaque |
| 8 | 5 ml Suniso 3GS | 0.2 | Transparent No Change |

We claim:

1. A method of distinguishing between an alkyl benzene and a naphthenic lubricant in a sample which comprises:
   a. adding a sufficient amount of 3,3-bis (p-hydroxyphenyl) phthalide to said sample and;
   b. observing the resulting turbidity against a blank, wherein said resulting turbidity indicates said lubricant is naphthenic whereas no turbidity indicates alkyl benzene lubricant.
2. A method according to claim 1 wherein said 3,3-bis (p-hydroxyphenyl) phthalide is a 1% solution in alcohol.
3. A method according to claim 2 wherein about 0.2 to about 5.0 ml of said 1% solution of 3,3-bis (p-hydroxyphenyl) phthalide is added to about 5 ml of said sample.
4. A method according to claim 3 wherein about 1 ml to about 3 ml of said 3,3-bis (p-hydroxyphenyl) phthalide is added to about 5 ml of said sample.

* * * * *